United States Patent
Ma et al.

(10) Patent No.: US 11,066,441 B2
(45) Date of Patent: Jul. 20, 2021

(54) METHOD FOR SEPARATING AND PURIFYING α2-MACROGLOBULIN FROM COHN FRACTION IV PRECIPITATION

(71) Applicant: ACADEMY OF MILITARY MEDICAL SCIENCES, Beijing (CN)

(72) Inventors: Yuyuan Ma, Beijing (CN); Chaoji Huangfu, Beijing (CN); Xiong Zhao, Beijing (CN); Maomin LV, Beijing (CN); Jingang Zhang, Beijing (CN); Junting Jia, Beijing (CN)

(73) Assignee: ACADEMY OF MILITARY MEDICAL SCIENCES, Beijing (CN)

( * ) Notice: Subject to any disclaimer, the term of this patent is extended or adjusted under 35 U.S.C. 154(b) by 418 days.

(21) Appl. No.: 15/760,715

(22) PCT Filed: Sep. 14, 2016

(86) PCT No.: PCT/CN2016/099059
§ 371 (c)(1),
(2) Date: Mar. 16, 2018

(87) PCT Pub. No.: WO2017/045617
PCT Pub. Date: Mar. 23, 2017

(65) Prior Publication Data
US 2018/0282368 A1    Oct. 4, 2018

(30) Foreign Application Priority Data

Sep. 17, 2015 (CN) .......................... 201510594293.5

(51) Int. Cl.
*C07K 1/36* (2006.01)
*C07K 1/14* (2006.01)
(Continued)

(52) U.S. Cl.
CPC ................ *C07K 1/36* (2013.01); *B01D 15/12* (2013.01); *B01D 15/34* (2013.01);
(Continued)

(58) Field of Classification Search
CPC ... C07K 1/36; C07K 1/14; C07K 1/22; C07K 1/34; C07K 1/16; C07K 1/30;
(Continued)

(56) References Cited

U.S. PATENT DOCUMENTS 6,193,891 B1 * 2/2001 Kent ....................... A61K 35/14
210/502.1
9,534,029 B2 * 1/2017 Brinkman .............. C07K 14/47

OTHER PUBLICATIONS

Sigma-Aldrich. "α2-Macroglobulin from human plasma," available at <http://www.sigmaaldrich.com/catalog/product/sigma/m6159?lang=en&region=>, accessed May 5, 2020, dated Mar. 27, 2013 via <http://www.archive.org>. (Year: 2013).*
(Continued)

*Primary Examiner* — Katherine Zalasky McDonald
(74) *Attorney, Agent, or Firm* — Scully, Scott, Murphy & Presser, P.C.

(57) ABSTRACT

The present invention discloses a method for separating and purifying α2-macroglobulin from Cohn Fraction IV precipitation, in which Cohn Fraction IV precipitation is treated by ammonium sulfate precipitation, zinc ion affinity chromatography, gel filtration, and ultrafiltration and concentration sequentially and thereby α2-macroglobulin is obtained finally. With the method provided in the present invention, purified α2-macroglobulin plasma protein that has a clinical application value is obtained, the Cohn Fraction IV precipitation is changed from a discarded material into a valuable material, and plasma is utilized comprehensively. In addition, the method is easy and simple to use, easy to scale up, and suitable for separation and purification of α2-macroglobulin at a large scale.

15 Claims, 2 Drawing Sheets

(51) Int. Cl.
*C07K 1/22* (2006.01)
*C07K 1/34* (2006.01)
*B01D 15/38* (2006.01)
*B01D 15/12* (2006.01)
*B01D 15/34* (2006.01)
*B01D 15/42* (2006.01)
*C07K 14/81* (2006.01)

(52) U.S. Cl.
CPC ....... *B01D 15/3828* (2013.01); *B01D 15/426* (2013.01); *C07K 1/14* (2013.01); *C07K 1/22* (2013.01); *C07K 1/34* (2013.01); *C07K 14/81* (2013.01); *C07K 14/8107* (2013.01)

(58) Field of Classification Search
CPC .... C07K 14/8107; C07K 14/81; B01D 15/38; B01D 15/3804; B01D 15/3828; B01D 15/424; B01D 15/426; B01D 15/12; B01D 15/125; B01D 15/24; B01D 15/08; B01D 2311/04; B01D 2311/02; B01D 61/14; B01D 61/16; B01D 61/145; B01D 61/58; G01N 30/02; G01N 30/04; G01N 30/06; G01N 30/14; G01N 30/84
See application file for complete search history.

(56) References Cited

OTHER PUBLICATIONS

BiteSizeBio, "How to design the perfect protein purification buffer," available at <https://bitesizebio.com/7893/how-to-design-the-perfect-protein-purification-buffer/>, published Nov. 3, 2011, 10 pages. (Year: 2011).*

GE Healthcare Life Sciences, "Protein sample preparation handbook," Dec. 2010, 123 pages. (Year: 2010).*

Ahrends et al. Application of displacement chromatography for the proteome analysis of a human plasma protein fraction. Journal of Chromatography A, 1217 (2010) 3321-3329. (Year: 2010).*

Odunuga et al. Ammonium sulfate precipitation combined with liquid chromatography is sufficient for purification of bovine serum albumin that is suitable for most routine laboratory applications. Biochemical Compounds 2013, 6 pages. (Year: 2013).*

Kurecki et al. Purification of human plasma α2 macroglobulin and α1 proteinase inhibitor using zinc chelate chromatography. Analytical Biochemistry, vol. 99, Issue 2, Nov. 1, 1979, pp. 415-420. (Year: 1979).*

* cited by examiner

METHOD FOR SEPARATING AND PURIFYING α2-MACROGLOBULIN FROM COHN FRACTION IV PRECIPITATION

FIELD OF THE INVENTION

The present invention relates to the technical field of separation and purification of blood products, in particular to a method for separating and purifying α2-macroglobulin from Cohn Fraction IV precipitation.

BACKGROUND ART

Cohn Fraction IV precipitation is a discarded material in production of plasma proteins, and may be abbreviated as Cohn IV precipitation. Cohn IV precipitation mainly contains proteins, which include many proteins that have potential values but are usually discarded as discarded material at present. Those proteins with potential values have very wide application prospects. For example, α1-antitrypsin can be used to treat patients who are suffering from α1-antitrypsin congenital deficiency and emphysema, and is a medicine approved by FDA; α2-macroglobulin can be used to treat radiation injuries, corneal injuries and keratitis; C1 esterase inhibitor can be used to treat hereditary angioneurotic edema; haptoglobin can be used to remove free hemoglobin in blood and prevent and treat hemolytic renal failure through intravenous infusion of haptoglobin or extracorporeal circulation of solidified haptoglobin; transferrin can be used to treat congenital atransferrinemia, and apotransferrin can be used to treat hemosiderosis; ceruloplasmin can promote erythropoiesis and treat anemia.

Wherein, α2-macroglobulin (α2-M) is an important protease inhibitor in human bodies, and its molecular weight is 720 kD. It is a tetramer consisting of four identical subunits, each of which consists of 1,451 amino acid, and has 8-11% sugar content, α2-M is mainly synthesized by liver cells; and the content of α2-M in the plasma in normal persons is 2-4 g/L. α2-M can remove excessive endogenous and extraneous proteases and thereby plays a role of a protease inhibitor in human body. Besides; α2-M has effects, including anti-radiation, anti-tumor, oxygen radical inhibition, participation in coagulation balance, and regulation of cytokine activity, etc.

α2-M was included in the Requirements for Biological Products (Trial, Edition 1990), and clinical indications mainly include radiation-induced local ulcer and injury of skin and mucosa, operative wound, ulcer and tissue necrosis at sites of radiotherapy, and keratitis, etc. Hence, there is an urgent need for a method for preparing high-purity α2-M at a high recovery rate in the field.

Early in 1955, α2-M was separated from human serum by Schultze for the first time. As the research on the biological features of α2-M was deepened and clinical applications were carried out, the research on processes for purification and preparation of α2-M became more and more extensive. Early in 1975, some researchers prepared high-purity α2-M through fractional precipitation of Rivanol method in conjunction with PEG precipitation and gel filtration, and the recovery rate of the process was as high as 60%. However, in the 1990s, producing blood products with Rivanol method was prohibited in China. As a result, the process was abandoned.

In 1978, some researchers prepared α2-M by affinity chromatography with cibacron blue dye, and the activity recovery rate of the method was as high as 75%. However, a limitation of that method was that haptoglobin 1-1 was required in the initial purification of plasma, but the donators of plasma that contained haptoglobin 1-1 only accounted for 10% of the plasma donators. Consequently, the raw material source for purification and preparation of α2-M was limited.

Some researchers prepared high-purity α2-M by chelating rabbit-anti-human α2-M antiserum to agarose medium and preparing by immunoaffinity chromatography. Though high-purity α2-M was obtained by immunoaffinity chromatography, the purification efficiency was very low. Therefore, that method was not suitable for preparation of α2-M in mass production. Later, some researchers purified α2-M by using PEG precipitation, affinity chromatography with cibacron blue dye, and two-step zinc ion affinity chromatography in combination, and the purification multiple was as high as 72.2, but the activity recovery rate was 31.1% only. In addition, some researchers prepared α2-M by separating fraction IV with a cold ethanol method and then preparing with an ammonium sulfate precipitation method. However, the purity of α2-M prepared with that method was about 40% only.

Owing to the above problems in the existing preparation and purification processes, the application of α2-M purification process in industrial production is limited. Though the Rivanol method process is suitable for use in mass production, it has been prohibited to use to produce blood products; the source of original plasma for affinity chromatography with cibacron blue dye is limited; immunoaffinity chromatography has low efficiency and is only applicable to preparation at a laboratory scale; α2-M prepared by ammonium sulfate precipitation solely has low purity, and can't meet the requirements for quality of blood products, etc. Besides, almost all of the purification processes employ plasma as the starting material. However, presently, in industrial production, plasma is mainly used to produce albumin, gamma globulin for intravenous injection, and coagulation factors, etc. If plasma is used as the raw material to prepare α2-M, the cost will be very high, and comprehensive utilization of plasma will be affected. At present, there is no process that utilizes Cohn Fraction IV precipitation as a raw material to prepare α2-M yet. If α2-M can be separated and purified from the discarded material produced in the production process of plasma proteins, the situation of comprehensive utilization of plasma will be improved.

CONTENTS OF THE INVENTION

The object of the present invention is to provide a method for separating and purifying α2-macroglobulin from Cohn Fraction IV precipitation, which is suitable for use in mass production.

In that method, Cohn Fraction IV precipitation is treated by ammonium sulfate precipitation, zinc ion affinity chromatography, gel filtration, and ultrafiltration and concentration sequentially, and finally α2-macroglobulin (α2-M) is obtained.

In the ammonium sulfate precipitation, the saturation of ammonium sulfate is 40-60%, preferably 45%-55%.

The ammonium sulfate precipitation is single precipitation, i.e., after ammonium sulfate is added, the mixture is stirred forth and then centrifuged for 15 min.

In the zinc ion affinity chromatography, the purification medium is zinc ion chelated high-flow rate agarose medium (Zn-IDA QZT 6FF).

In the zinc ion affinity chromatography, the eluent may be one of 0.1M $Na_2EDTA$ with pH=6.5-7.0, 20 mM Tris+0.1M NaCl+0.1-0.5M imidazole with pH-7.4, 0.02M Tris+0.5M NaCl at pH=4.5-5.0, and 20 mM Tris+0.1M NaCl+0.01-0.05M histidine with pH=7.4.

In the gel filtration, the filtering medium may be Polyacrylamide-dextran gel Sephacryl-200 HR, Polyacrylamide-dextran gel Sephacryl-300 HR, agarose gel (Superose prep grade or Superose 12), or cross-link dextran (G-200 Sephadex G-200).

In the ultrafiltration and concentration, the ultrafiltration membrane has molecular weight cutoff within a range of 30-500 kD, preferably is an ultrafiltration membrane that has 50-100 kD pore size.

Specifically, the method comprises the following steps:
a) ammonium sulfate precipitation: dissolving Cohn Fraction IV precipitation in distilled water in volume equal to 8-12 times of the volume of the Cohn Fraction IV precipitation, obtaining filtrate through compression filtration, adding ammonium sulfate to the filtrate till the saturation is 40%-60%, centrifuging the resultant mixture to obtain precipitate and supernatant, and then discarding the supernatant;
b) zinc ion affinity chromatography: dissolving the precipitate obtained in the step a) in equilibrium buffer to obtain a solution of dissolved precipitate, treating the solution by zinc ion affinity chromatography, stopping elution when a protein peak drops to the baseline, and then collecting eluent produced through affinity chromatography; wherein, zinc ion chelated high flow-rate agarose medium (Zn-IDA (AZT 6FF) is selected as the purification medium, and preferably the volume of the equilibrium buffer used to dissolve the precipitate is ½ of the volume of the compression leachate in the step a);
c) gel filtration: filtering the eluent obtained through affinity chromatography in the step b) by gel filtration, and collecting eluent with the first protein peak after gel filtration;
d) ultrafiltration and concentration: concentrating the protein concentration in the eluent obtained through gel filtration in the step c) to 4.5-5.5%, and then using a 0.22 μm filter to carry out sterile filtration, so as to obtain the target protein;
preferably, the equilibrium buffer used to dissolve the precipitate in the step b) is buffer solution 0.02M Tris+0.5M NaCl with pH=6.0-7.0; the eluent in the step b) is 0.1M Na$_2$EDTA with pH=6.5-7.0.

The zinc ion affinity chromatography in the step b) mainly comprises the following steps: i) column loading: loading the purification medium into a chromatography column; ii) purification medium buffering: buffering the purification medium with the equilibrium buffer; iii) sample loading: pumping the solution of dissolved precipitate into the chromatography column; iv) rinsing/leaching: leaching off the protein that is not coupled to the purification medium with the equilibrium buffer; v) elution: eluting off the proteins coupled to the purification medium with the eluent;
the gel filtration in the step c) mainly comprises the following steps: i) column loading: loading the filtering medium into a chromatography column; ii) filtering medium buffering: buffering the filtering medium with the equilibrium buffer; iii) sample loading: pumping the eluent obtained through affinity chromatography in the step b) into the chromatography column; iv) leaching: leaching off the target protein α2-macroglobulin with the equilibrium buffer;
preferably, the equilibrium buffer used in the purification medium buffering and leaching in the step b) and the equilibrium buffer used in the filtering medium buffering and leaching in the step c) are buffer solution 0.02M Tris+0.5M NaCl with pH=6.0-7.0.

Before the step b) is executed, the precipitate obtained in the step a) is dissolved in a dialysis solution for desalination by ultrafiltration, wherein; the dialysis solution is buffer solution 0.02M Tris+0.5M NaCl with pH=6.0-7.0; preferably, the ultrafiltration membrane used in the desalination by ultrafiltration has a molecular weight cutoff within a range of 30-500 kD, preferably is an ultrafiltration membrane that has 50-100 kD pore size.

The present invention further provides α2-macroglobulin, which is obtained by separation and purification from Cohn Fraction IV precipitation with the method described above, at purity not lower than 94%; in addition, the recovery rate of the method is not lower than 45%.

The present invention further provides α2-macroglobulin obtained by separation and purification from Cohn Fraction IV precipitation with the method described above.

Compared with the prior art, the present invention attains the following beneficial effects:

In the present invention, Cohn Fraction IV precipitation is selected as the starting raw material for separation and purification to obtain α2-M. The raw material is produced in the production process of albumin with a cold ethanol method in the industry. At present, the Cohn Fraction IV precipitation is usually disposed as an industrial waste material. Therefore, the price of the raw material is very low. In the present invention, since α2-M with medical value is prepared from the discarded material, the production cost is reduced, and the comprehensive utilization of plasma and economic benefit are improved. On that basis, high-purity α2-M is prepared with salt precipitation, affinity chromatography, and gel filtration methods in combination in the separation and purification process, wherein, the Cohn Fraction IV separation is separated crudely in the ammonium sulfate precipitation step so that almost half of contaminant proteins are removed; then α2-M is concentrated specifically by zinc ion affinity chromatography; finally α2-M is separated from small-molecule miscellaneous proteins by gel filtration with zeolite. In the affinity chromatography, metal-chelated high flow-rate agarose (Zn-IDA QZT 6FF) is used as a substrate, which is highly resistant to alkalis, has high linear flow rate, and is suitable for industrial production. The method provided in the present invention is easy and simple to use, and the purity of α2-M obtained through separation and purification is as high as 90% or above, which meets the requirements for quality of blood products; with the method, the activity recovery rate of α2-M is usually higher than 50%. The method is suitable for used in mass production.

DETAILED DESCRIPTION OF THE EMBODIMENTS

Figure 1:
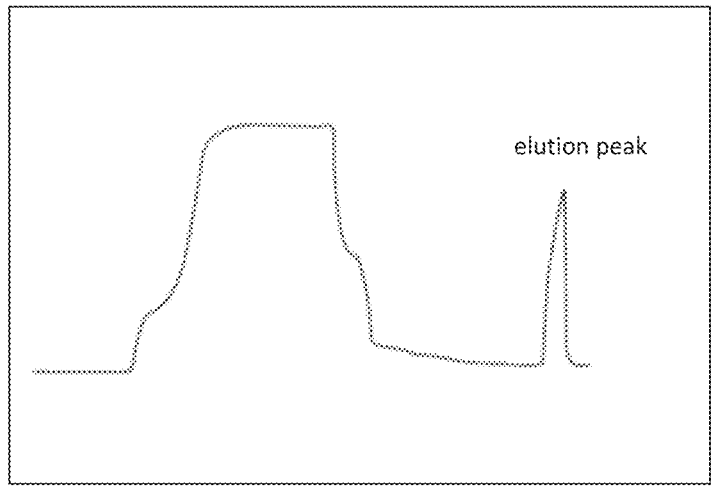
FIG. 1 is a chromatogram of the α2-M obtained by separation and purification through zinc ion affinity chromatography.

The method for separating and purifying α2-macroglobulin from Cohn Fraction IV precipitation provided in the present invention employs a process in which Cohn Fraction IV precipitation is treated by ammonium sulfate precipitation, zinc ion affinity chromatography, gel filtration, and ultrafiltration and concentration sequentially and thereby α2-macroglobulin is obtained finally.

Specifically, the method comprises the following steps:

a) ammonium sulfate precipitation: dissolving Cohn Fraction IV precipitation in distilled water (the mass-to-volume ratio (g:mL) of Cohn Fraction IV precipitation to distilled water is 1:(8-12)), obtaining filtrate through compression filtration, adding ammonium sulfate to the filtrate slowly (for about 1 h) till the saturation is 40%-60%, preferably 45%-55%, centrifuging the resultant mixture at 8,000 g/min. centrifugal rate for 15 min. to obtain precipitate and supernatant, and then discarding the supernatant.

b) zinc ion affinity chromatography: dissolving the precipitate obtained in the step a) with equilibrium buffer (0.02M Tris+0.5M NaCl with pH=6.0-7.0) to obtain a solution of dissolved precipitate (obtained by adding the precipitate into the equilibrium buffer and stirring), wherein, the volume of the equilibrium buffer is ½ of the volume of the compression leachate obtained in the step a); then, performing zinc ion affinity chromatography, till the protein peak drops to the baseline; at that point, stopping the elution and collecting the eluent produced through affinity chromatography.

The zinc ion affinity chromatography is performed with a protein purifier AKTA Purifier from GE, and mainly consists of the following steps: i) column loading: loading a purification medium into a chromatography column (the volume of the purification medium is 1 column volume (1 CV)), and connecting the chromatography column to the protein purifier; ii) purification medium buffering: buffering the purification medium with about 5CV equilibrium buffer; iii) sample loading: pumping the solution of dissolved precipitate into the chromatography column, so that the target protein α2-M can be coupled to the purification medium extensively; iv) rinsing/leaching leaching off the protein that is not coupled to the purification medium with the equilibrium buffer, till only protein coupled to the purification medium is left in the purification medium when the protein is leached to the baseline, wherein, usually about 8-10CV equilibrium buffer is required for the leaching; v) elution: eluting off the proteins coupled to the purification medium with the eluent, wherein, usually 1CV eluent is required.

A zinc ion chelated high flow-rate agarose medium (Zn-IDA QZT 6FF) is selected as the purification medium, the volume ratio of the purification medium to the solution of dissolved precipitate is determined according to the concentration of proteins in the solution of dissolved precipitate; in the present invention, the volume ratio of the purification medium to the solution of dissolved precipitate is about 1:5. An equilibrium buffer (0.02M Tris+0.5M NaCl with pH=6.0-7.0) is used in the purification medium buffering and leaching procedures, and 0.1M Na$_2$EDTA with pH=6.5-7.0 is used as the eluent.

c) gel filtration: performing gel filtration of the eluent obtained through affinity chromatography in the step b). The gel filtration realizes separation and purification of proteins under a principle that the retention times of proteins in different molecular weights in the filtering medium are different from each other, i.e., the higher the molecular weight of a protein is, the earlier the protein is leached off. Owing to the fact that α2-M has the highest molecular weight among the proteins, only the first protein peak has to be collected. Similar to the zinc ion affinity chromatography process, this process also consists of column loading, filtering medium buffering, sample loading, and leaching steps, and is executed with the protein purifier AKTA Purifier from GE, which can detect the concentrations of proteins in the eluent and plot a protein peak diagram automatically according to the concentrations. In the operation, since the target protein α2-M is leached off first, the eluent with the first protein peak is collected according to the indication of protein peak in the instrument, and the collection is stopped once the second peak occurs.

Wherein, the filtering medium is one of Polyacrylamide-dextran gel Sephacryl-200 HR, Polyacrylamide-dextran gel Sephacryl-300 HR, Superose 12 (agarose gel), Superose prep grade (agarose gel), and Sephadex G-200 (cross-link dextran G-200), the volume of the eluent produced through affinity chromatography usually is 1-3% of the volume of the filtering medium, and an equilibrium buffer (0.02M Tris+0.5M NaCl with pH=6.0-7.0) is used in the filtering medium buffering and the leaching.

d) ultrafiltration and concentration: performing ultrafiltration and concentration of the eluent obtained through gel filtration in the step c), to concentrate to 4.5-5.5% protein concentration; then, performing sterile filtration with a 0.22 μm filter; thus; the target protein α2-M product is obtained, and is in liquid state.

The ultrafiltration membrane has a molecular weight cutoff within a range of 30-500 kD, and preferably is an ultrafiltration membrane that has 50-100 kD pore size.

In the method described above, before the step b) is executed, preferably the precipitate obtained in the step a) is dissolved in a dialysis solution for desalination by ultrafiltration, wherein, the ultrafiltration membrane has molecular weight cutoff within a range of 30-500 kD, and the dialysis solution is buffer solution 0.02M Tris+0.5M NaCl with pH=6.0-7.0.

EXAMPLES

α2-M in Cohn Fraction IV precipitation is separated and purified with the method described above, and some parameters in the method are adjusted (see Table 1). Then, the obtained products are identified by mass spectrometry, as shown in Table 2. Next, the purity and activity recovery rate of the obtained α2-M are detected, and the results are shown in Table 3.

Figure 2:
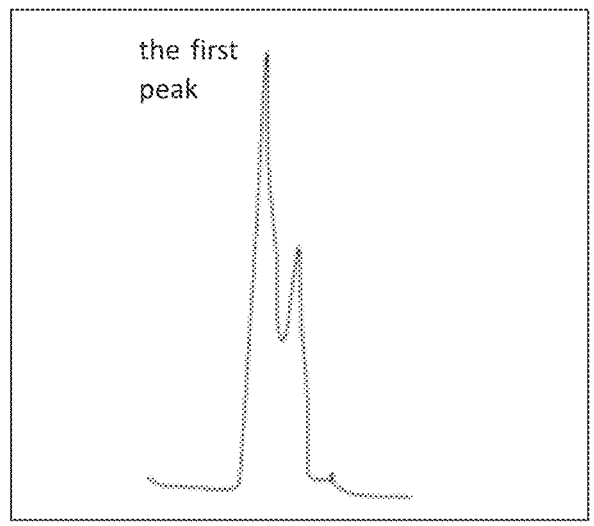
FIG. 2 is a chromatogram of the α2-M obtained by separation and purification through gel filtration.
Figure 3:
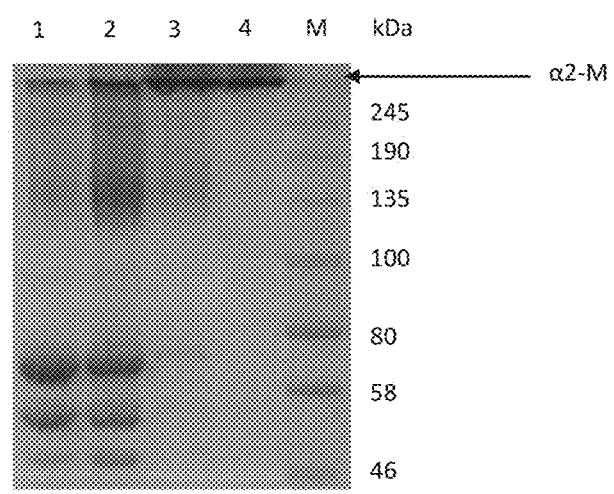
FIG. 3 is a non-reduced electrophoregram of the α2-M obtained in SDS-PAGE identification.

Taking Example 1 as an example, FIGS. 1-3 show chromatograms of α2-M obtained through separation and purification with the method in the example 1, wherein, FIG. 3 is a non-reduced chromatogram of α2-M identified by SDS-PAGE, M is molecular weight marker, the bands 1-3 respectively represent the compression leachate in the step a), the solution of dissolved precipitate in the step b), and the eluent obtained through affinity chromatography in the step b), and the band 4 represents the eluent obtained in the step c), i.e., the first peak of Sephacryl-200 HR.

TABLE 1

Results of α2-M Separated and Purified from Cohn Fraction IV Precipitation with Different Parameters

| | Parameter | Example 1 | 2 | 3 | 4 | 5 | 6 | 7 | 8 | 9 |
|---|---|---|---|---|---|---|---|---|---|---|
| Step a) | Cohn Fraction IV precipitation (g) | 100 | 1000 | 300 | 500 | 800 | 1000 | 1000 | 500 | 500 |
| | Distilled water (mL) | 800 | 11000 | 2700 | 4500 | 7200 | 10000 | 10000 | 4500 | 4500 |
| | Saturation of ammonium sulfate (%) | 40 | 60 | 45 | 50 | 55 | 50, 50, 50, 40, 55 | 50, 40, 55 | 30 | 70 |
| | Conditions of centrifuge | 8000 g/min 15 min | | 8000 g/min 10 min | 7000 g/min 15 min | 6000 g/min 20 min | 8000 g/min 20 min | | 7000 g/min 15 min | |
| Desalination by ultrafiltration | Pore size (kD) | 30 | 500 | 100 | 300 | 300 | 500 | 500 | 300 | 300 |
| Step b) | pH of equilibrium buffer | 7.0 | 6.0 | 6.4 | 6.5 | 6.8 | 6.0 | 6.0 | 6.5 | 6.5 |
| | pH of eluent | 7.0 | 6.5 | 6.8 | 6.8 | 6.8 | 6.8 | 6.8 | 6.8 | 6.8 |
| | Eluent | | | | | 0.1M Na$_2$EDTA | | | | |
| | Purification medium | | | Zn-IDA QZT 6FF | | | Zn-Sepharose CL6B | | Zn-IDA QZT 6FF | |
| Step c) | pH of equilibrium buffer | 6.0 | 7.0 | 6.2 | 6.5 | 6.8 | None | None | 6.5 | |
| | Filtering medium | | Sephacryl-200 HR | | Sephacryl-300 HR | | | | Sephacryl-300 HR | |
| Step d) | Concentration of protein (%) | 4.5 | 5.5 | 5.5 | 4.8 | 5.2 | 5.2 | 5.0 | 4.9 | 5.3 |
| | Ultrafiltration pore size (kD) | 30 | 100 | 100 | 300 | 300 | 100 | 100 | 300 | 300 |

The purpose of mass spectrometry is to identify whether the prepared protein is the target protein, by analyzing the protein in the band 4 shown in FIG. 3, comparing the peptide fragments of the protein with the peptide fragments in the database, and sorting by the degree of matching. Higher degree of matching indicates higher probability that the protein obtained through purification is the matching protein. The number on the left is the gi no. of the corresponding peptide fragment on the right, and the gi no. may be searched in pubmed to obtain specific information of the corresponding peptide fragment. The results are obtained as shown in Table 2. According to Table 2: the three peptide fragments at the highest degree of matching belong to human α2-macroglobulin (the second gi no. and the third gi no, are searched in pubmed to obtain relevant information), the keratin identified by the seventh gi no. and the eighth gi no. is protein in the finger skin attached to the sample, and is an experimental error rather than a protein prepared in the experiment. All other identified proteins are essentially α2-macroglobulin with other properties. Hence, it can be ascertained through the experiment that the protein obtained through purification with the method described above is right α2-macroglobulin.

TABLE 2

Translation Result of Gi Nos. in the
Mass Spectrometry Result of the Band 4 in FIG. 3

| 1 | gi|177870 | α2-M precursor (human) |
| 2 | gi|377656551 | Chain A, α2-M |
| 3 | gi|224053 | α2-M |
| 4 | gi|426371570 | α2-M analogue (gorilla) |
| 5 | gi|332232615 | α2-M (black gibbon) |
| 6 | gi|28317 | Unnamed protein (human) |
| 7 | gi|11935049 | Keratin (human) |
| 8 | gi|375314779 | Keratin (human) |
| 9 | gi|403269387 | α2-M analogue (saimiri) |
| 10 | gi|390467482 | α2-M (marmoset) |

The mass spectrometry identification result in Table 2 indicates that the band 4 is the α2-M obtained through purification with the method provided in the present invention. The chromatograms and mass spectrometry identification results of α2-M obtained through separation and purification with the methods in examples 2-5 are the same as those in the FIGS. 1-3 and Table 2, and will not be detailed further here.

Reference Example 1

The reference example 1 is the example 6. The specific operations are: 1,000 g Cohn Fraction IV precipitation is dissolved in 10,000 ml distilled water, the solution is stirred for 1 h and then filtered, and thereby 9,500 ml filtrate is obtained. Ammonium sulfate solution at 100% saturation in the same volume is added to the filtrate, and the mixture is stirred for 1 h and then aged overnight at 4° C. Precipitate A and supernatant A are obtained through centrifugal separation, the precipitate A is dissolved in 5,000 ml ammonium sulfate solution at 50% saturation, and the resultant solution is stirred for 1 h and then centrifuged, and thereby precipitate B and supernatant B are obtained. The precipitate B is dissolved in 4,000 ml ammonium sulfate solution at 50% saturation, and the resultant solution is centrifuged and thereby precipitate C and supernatant C are obtained; the precipitate C is dissolved in 3,000 ml distilled water, solid ammonium sulfate is added to the resultant solution at a ratio of 243 g/L, so that the saturation reaches 40%, and then the solution is treated by centrifugal separation, and thereby precipitate D and supernatant D are obtained. Solid ammonium sulfate is added to the supernatant D at a ratio of 97 g/L, so that the degree of saturation of ammonium sulfate reaches 55%, and then the solution is stirred for 1 h and centrifuged, the obtained precipitate E is dissolved in 1,000 ml buffer solution (0.02M Tris+0.15M NaCl, with pH=6.0), ultrafiltration is carried out with a 500 kDa ultrafiltration membrane for desalination, the obtained 600 ml trapped fluid is treated by zinc ion affinity chromatography, the material is leached further with the buffer solution after sample loading, till the protein peak is close to the baseline; then, the material is eluted with an eluent (0.1M Na$_2$EDTA, with pH=6.8), till the protein peak drops to the baseline. About 150 ml eluent rich in α2-M is collected.

Reference Example 2

In the reference example 2, the method put forth by Qiming Peng et al. (separation and purification of α2-macroglobulin from human plasma, Progress in Biochemistry and Biophysics, 1986, 3:69-72) is used, and human plasma is used as the raw material; first, the plasma is processed by precipitation with 4%-12% polyethylene glycol, and then α2-macroglobulin is prepared through purification by zinc ion affinity chromatography, affinity chromatography with blue agarose, and secondary zinc ion affinity chromatography sequentially.

Reference Example 3

In the reference example 3, the method put forth by G. D. Virca et al. (Purification of Human α2-Macrolobulin by Chromatography on Cibacron Blue Sepharose, Analytical Biochemistry, 1978, 89:274-278), and haptoglobin 1-1 is used as the raw material, and treated by affinity chromatography with blue agarose and gel filtration sequentially.

Reference Example 4

In the reference example 4, α2-macroglobulin is prepared through ammonium sulfate fractional precipitation with the α2-macroglobulin preparation method specified in the China Requirements for Biological Products (Trial, Edition 1990).

The concentration, specific activity, recovery rate and purity of the proteins obtained in the examples 1-9 in the present invention are measured, and the detection results are recorded in Table 3. The activity of α2-M is measured on the basis of the quantity of trypsin inhibited by unit volume of sample (μg/ml); the specific activity (μg/mg) is equal to the activity divided by protein content, and represents the quantity of trypsin inhibited by per milligram of protein; the purity is measured with purity analysis software Band Scan 5.0.

TABLE 3

Summary of Purification Test Result

| | Concentration of Protein (%) | Specific Activity (μg/mg) | Recovery Rate (%) | Purity (%) |
|---|---|---|---|---|
| Example 1 | 4.5 | 14.4 | 55.3 | 95.1 |
| Example 2 | 5.5 | 13.3 | 48.5 | 94.4 |
| Example 3 | 5.0 | 14.6 | 53.2 | 96.4 |
| Example 4 | 4.8 | 14.2 | 55.6 | 95.2 |
| Example 5 | 5.5 | 13.7 | 58.8 | 94.8 |
| Example 6/ reference example 1 | 5.2 | 14.1 | 23.4 | 96.5 |
| Example 7 | 5.3 | 10.3 | 39.4 | 70.5 |
| Example 8 | 5.1 | 14.4 | 30.3 | 95.9 |
| Example 9 | 5.0 | 11.7 | 65.5 | 80.5 |
| Reference example 2 | 4.8 | 12.9 | 24.5 | 93.9 |
| Reference example 3 | 4.8 | 9.8 | 70.0 | 67.8 |
| Reference example 4 | 5.0 | 5.5 | 75.2 | 35.6 |

According to Table 3: the specific activity, recovery rate, and purity are stable in examples 1-5. For example, the protein concentration is about 5.0%; the specific activity, recovery rate, and purity are about 14.0 μg/mg, 54%, and 95% respectively.

When the eluent in the example 6 (i.e., reference example 1) is ultra-filtered to 20 ml, the concentration of the obtained α2-M protein is 5.2%, the specific activity is 14.1 μg/mg, and the recovery rate is 23.4%. In the reference example 1, α2-M is prepared with the method disclosed in an English literature (Purification of Human Plasma α2 Macroglobulin and α1 Proteinase Inhibitor Using Zinc Chelate Chromatography, ANALYTICAL BIOCHEMISTRY, 1979, 99:415-420), except that the starting material used in the English document is plasma, while the starting material used in the reference example 1 is Fraction IV precipitation. The differences between the method in the reference example 1 and the method provided in the present invention mainly include: (1) in the present invention, a single pass of ammonium sulfate precipitation is used, and the reaction time in the ammonium sulfate precipitation step is shorter (1 h stirring followed by 15 min. centrifugation), a fractional ammonium sulfate precipitation method (i.e., several passes of ammonium sulfate precipitation) is used, and the reaction time is longer (overnight); the recovery rate in the reference example 1 is lower, because the activity α2-M may be deteriorated by ammonium sulfate; (2) though the method provided in the present invention has an additional step of gel filtration compared with the method in the reference example 1, the protein is not deactivated in the gel filtration step, because the reaction conditions of the gel filtration are mild. In summary, in the method in the reference example 1; at the beginning of purification, ammonium sulfate precipitation is used for several times to purify α2-M to achieve high purity before zinc ion affinity chromatography, but the loss of activity of α2-M is severe, and the reaction time is long. In contrast, in the present invention, only one pass of ammonium sulfate precipitation is used, and the reaction time is shorter. Though a gel filtration step is added after zinc ion affinity chromatography, the overall purification time is short, and the recovery rate is higher than that in the reference example 1.

Though the specific activity and purity achieved in the example 6 are comparable to those achieved in the examples 1-5 (14.1 μg/mg and 96.5% respectively), the recovery rate in the example 6 is too low (only 23.4%). Therefore, the method in the example 6 is not suitable for mass production. Compared with the method in the example 6, the method in the example 7 simplifies the ammonium sulfate precipitation step, and, as a result, the activity and recovery rate are improved (to 39.4%), but the purity is relatively low (only 70.5%). In the examples 8 and 9, the experimental procedures in the present invention are used essentially, but the selected saturation of ammonium sulfate is too high or too low; consequently, a satisfactory result in terms of purity and recovery rate can't be obtained in the product. For example, the purity in the example 8 is comparable to that in the examples 1-5, but the recovery rate in the example 8 is too low; though the recovery rate in the example 9 is higher, the purity is too low, only 80.5%. In the reference examples 2-4, the same defect also exists, i.e., a satisfactory result in terms of purity and recovery rate can't be obtained; though the purity in the reference example 2 is comparable to those in the examples 1-5, the recovery rate is too low; though the recovery rate in the reference example 3 is higher, the purity is too low; the purity in the reference example 4 is even lower.

Hence, with the method provided in the present invention, α2-M plasma protein that has a clinical application value is obtained through purification from Cohn Fraction IV precipitation that is regarded as an industrial waste at present by salt precipitation, affinity chromatography and gel filtration in combination. Thus, the Cohn Fraction IV precipitation is changed from a discarded material into a valuable material, and plasma is utilized comprehensively. In addition, the method is easy and simple to use, easy to scale up, and suitable for separation and purification of α2-M at a large scale. With the method provided in the present invention, the recovery rate in the separation and purification is about 50%, and the purity is about 95%. In contrast, in the processes reported in other technical literatures, high recovery rate and high purity can't be achieved at the same time. Therefore, the present invention has bright application prospects.

INDUSTRIAL APPLICABILITY

With the method provided in the present invention, α2-macroglobulin plasma protein that has a clinical application value can be separated and purified from Cohn Fraction IV precipitation, and the Cohn Fraction IV precipitation is changed from a discarded material into a valuable material; in addition, the method is easy and simple to use, easy to scale up, and is suitable for separation and purification of α2-macroglobulin at a large scale and suitable for industrial application.

The invention claimed is:

1. A method for separating and purifying α2-macroglobulin from a Cohn Fraction IV precipitation, the method comprising subjecting the Cohn Fraction IV precipitation to the following sequential steps:
   (a) ammonium sulfate precipitation;
   (b) zinc ion affinity chromatography;
   (c) gel filtration; and
   (d) ultrafiltration and concentration;
   thereby obtaining α2-macroglobulin, wherein the ultrafiltration step utilizes an ultrafiltration membrane having a molecular weight cutoff within a range of 30-500 kD, and
   wherein, in the ammonium sulfate precipitation, the saturation of the ammonium sulfate is 40-60%, and the ammonium sulfate precipitation consists of a single precipitation.

2. The method according to claim 1, wherein, in the ammonium sulfate precipitation, the saturation of the ammonium sulfate is 45%-55%.

3. The method according to claim 1, wherein the single precipitation consists essentially of adding ammonium sulfate to the Cohn Fraction IV precipitation to form a mixture, stirring the mixture for 1 hour and then centrifuging the mixture for 15 minutes.

4. The method according to claim 1, wherein the zinc ion affinity chromatography employs zinc ion chelated agarose medium as a purification medium.

5. The method according to claim 1, wherein the zinc ion affinity chromatography employs an eluent selected from the group consisting of 0.1M $Na_2EDTA$ with pH=6.5-7.0, 20 mM Tris+0.1M NaCl+0.1-0.5M imidazole with pH=7.4, 0.02M Tris+0.5M NaCl at pH=4.5-5.0, and 20 mM Tris+0.1M NaCl+0.01-0.05M histidine with pH=7.4.

6. The method according to claim 1, wherein the gel filtration employs a filtering medium selected from the group consisting of polyacrylamide-dextran gel, agarose gel, and crosslinked dextran.

7. The method according to claim 1, wherein, in the ultrafiltration and concentration steps, the ultrafiltration membrane has a molecular weight cutoff within a range of 50-100 kD.

8. The method according to claim 1, comprising the following steps:
   a) single precipitation consisting essentially of: dissolving Cohn Fraction IV precipitation in distilled water in volume equal to 8-12 times of the volume of the Cohn Fraction IV precipitation, obtaining filtrate through compression filtration, adding ammonium sulfate to the filtrate until the saturation is 40%-60%, centrifuging the resultant mixture to obtain precipitate and supernatant, and then discarding the supernatant;
   b) zinc ion affinity chromatography which comprises: dissolving the precipitate obtained in step a) in equilibrium buffer to obtain a solution of dissolved precipitate, loading the solution into a column containing a zinc ion affinity chromatography medium and eluting the column with eluent, stopping elution when a protein peak drops to the baseline, and collecting the eluent from the column; wherein the zinc ion affinity chromatography medium is zinc ion chelated agarose medium;
   c) gel filtration which comprises: filtering the eluent obtained through affinity chromatography in step b) by gel filtration, and collecting eluent with the first protein peak after gel filtration; and
   d) ultrafiltration and concentration which comprises: concentrating the protein concentration in the eluent obtained through gel filtration in step c) to 4.5-5.5%, and then using a 0.22 μm filter to carry out sterile filtration, so as to obtain the target protein.

9. The method according to claim 8, wherein, the zinc ion affinity chromatography in step b) comprises the following steps: i) column loading: loading the zinc ion affinity chromatography medium into a zinc ion affinity chromatography column; ii) zinc ion affinity chromatography medium buffering: eluting the zinc ion affinity chromatography medium with the equilibrium buffer, which functions as an eluent; iii) sample loading: pumping the solution of dissolved precipitate into the zinc ion affinity chromatography column; iv) rinsing: leaching off the protein that is not coupled to the zinc ion affinity chromatography medium with the equilibrium buffer; v) elution: eluting off the proteins coupled to the zinc ion affinity chromatography medium with the eluent; and
   the gel filtration in step c) comprises the following steps: i) column loading: loading a filtering medium into a gel filtration chromatography column; ii) filtering medium buffering: buffering the filtering medium with a gel filtration equilibrium buffer; iii) sample loading: pumping the eluent obtained through affinity chromatography in step b) into the gel filtration chromatography column; iv) leaching: leaching off the target protein α2-macroglobulin with the gel filtration equilibrium buffer.

10. The method according to claim 8, wherein, before step b) is performed, the precipitate obtained in step a) is dissolved in a dialysis solution and desalinated by ultrafiltration, wherein, the dialysis solution is buffer solution 0.02M Tris+0.5M NaCl with pH=6.0-7.0.

11. The method according to claim 8, wherein, in step b), the volume of the equilibrium buffer used to dissolve the precipitate is one-half of the volume of the supernatant in step a).

12. The method according to claim 8, wherein the equilibrium buffer used to dissolve the precipitate in step b) is buffer solution 0.02M Tris+0.5M NaCl with pH=6.0-7.0, and the eluent in step b) is 0.1M $Na_2EDTA$ with pH=6.5-7.0.

13. The method according to claim 9, wherein the equilibrium buffer in step b) and the gel filtration equilibrium buffer in step c) is 0.02M Tris+0.5M NaCl with pH=6.0-7.0.

14. The method according to claim 10, wherein an ultrafiltration membrane used in the desalination by ultrafiltration has a molecular weight cutoff within a range of 30-500 kD.

15. The method according to claim 10, wherein an ultrafiltration membrane used in the desalination by ultrafiltration has a 50-100 kD pore size.

* * * * *